(12) United States Patent
Demehri et al.

(10) Patent No.: US 10,117,738 B2
(45) Date of Patent: Nov. 6, 2018

(54) ATRAUMATIC TIP GEOMETRY FOR INDWELLING DEVICES

(71) Applicant: THE REGENTS OF THE UNIVERSITY OF MICHIGAN, Ann Arbor, MI (US)

(72) Inventors: Farokh R. Demehri, Ann Arbor, MI (US); Daniel H. Teitelbaum, Ann Arbor, MI (US); Jonathan E. Luntz, Ann Arbor, MI (US); Brent Utter, Easton, PA (US); Diann Erbschloe Brei, Milford, MI (US); Jennifer Freeman, Cambridge, MA (US)

(73) Assignee: The Regents of The University of Michigan, Ann Arbor, MI (US)

( * ) Notice: Subject to any disclaimer, the term of this patent is extended or adjusted under 35 U.S.C. 154(b) by 184 days.

(21) Appl. No.: 15/005,218

(22) Filed: Jan. 25, 2016

(65) Prior Publication Data
US 2016/0213461 A1 Jul. 28, 2016

Related U.S. Application Data

(63) Continuation-in-part of application No. 14/718,175, filed on May 21, 2015.
(Continued)

(51) Int. Cl.
*A61F 2/04* (2013.01)
*A61B 17/02* (2006.01)
(Continued)

(52) U.S. Cl.
CPC .............. *A61F 2/04* (2013.01); *A61B 17/02* (2013.01); *A61M 29/02* (2013.01);
(Continued)

(58) Field of Classification Search
CPC .............. A61B 17/02; A61B 17/12045; A61B 2017/0057; A61B 2017/00818;
(Continued)

(56) References Cited

U.S. PATENT DOCUMENTS

| 4,840,690 A * | 6/1989 | Melinyshyn ........... A61B 17/11 156/242 |
| 4,950,226 A | 8/1990 | Barron |

(Continued)

FOREIGN PATENT DOCUMENTS

| EP | 1796553 A2 | 6/2007 |
| SU | 1650147 A1 | 5/1991 |

(Continued)

OTHER PUBLICATIONS

International Search Report and Written Opinion regarding PCT/US2016/014688 dated Jun. 10, 2016.
(Continued)

*Primary Examiner* — Jocelin Tanner
(74) *Attorney, Agent, or Firm* — Harness, Dickey & Pierce, P.L.C.

(57) ABSTRACT

An indwelling device for insertion in a biological tubular structure comprising an elongated device having a body and opposing ends. The body has a bending stiffness transverse to a longitudinal axis that is greater than a stiffness of the biological tubular structure. An atraumatic tip member, having a proximal end and a distal end, extends from the end of the elongated device. The proximal end has a first bending stiffness transverse to a longitudinal axis and the distal end has a second bending stiffness transverse to the longitudinal axis, wherein the second bending stiffness being less than the first bending stiffness.

14 Claims, 8 Drawing Sheets

Related U.S. Application Data (60) Provisional application No. 62/106,859, filed on Jan. 23, 2015.

(51) Int. Cl.
  *A61M 29/02* (2006.01)
  *A61B 17/12* (2006.01)
  *A61B 17/00* (2006.01)

(52) U.S. Cl.
  CPC .......... *A61B 17/12045* (2013.01); *A61B 2017/00557* (2013.01); *A61B 2017/00818* (2013.01); *A61B 2017/12127* (2013.01); *A61F 2002/045* (2013.01); *A61F 2250/001* (2013.01); *A61F 2250/0018* (2013.01); *A61F 2250/0029* (2013.01); *A61F 2250/0059* (2013.01); *A61F 2250/0069* (2013.01)

(58) Field of Classification Search
  CPC ..... A61B 2017/12127; A61F 2002/045; A61F 2250/001; A61F 2250/0018; A61F 2250/0029; A61F 2250/0059; A61F 2250/0069; A61M 25/0068; A61M 25/0069
  See application file for complete search history.

(56) References Cited

U.S. PATENT DOCUMENTS

| | | | |
|---|---|---|---|
| 5,161,547 A | 11/1992 | Tower | |
| 5,205,830 A | 4/1993 | Dassa et al. | |
| 5,211,654 A | 5/1993 | Kaltenbach | |
| 5,364,396 A | 11/1994 | Robinson et al. | |
| 5,415,660 A | 5/1995 | Campbell et al. | |
| 5,634,901 A | 6/1997 | Alba et al. | |
| 5,662,583 A | 9/1997 | Khouri | |
| 5,681,309 A | 10/1997 | Ross, Jr. et al. | |
| 5,693,014 A | 12/1997 | Abele et al. | |
| 5,700,252 A | 12/1997 | Klingenstein | |
| 5,769,870 A * | 6/1998 | Salahieh | A61B 17/11 606/108 |
| 5,836,864 A | 11/1998 | Clark, Jr. | |
| 5,902,304 A | 5/1999 | Walker et al. | |
| 5,911,715 A * | 6/1999 | Berg | A61M 25/0009 138/125 |
| 5,916,193 A * | 6/1999 | Stevens | A61M 1/3659 604/28 |
| 5,947,104 A | 9/1999 | Li | |
| 6,030,386 A | 2/2000 | Taylor et al. | |
| 6,293,920 B1 | 9/2001 | Sweezer et al. | |
| 6,319,233 B1 | 11/2001 | Jansen et al. | |
| 6,336,929 B1 | 1/2002 | Justin | |
| 6,355,031 B1 | 3/2002 | Edwards et al. | |
| 6,358,283 B1 | 3/2002 | Hogfors et al. | |
| 6,368,315 B1 * | 4/2002 | Gillis | A61M 25/0026 604/523 |
| 6,375,638 B2 | 4/2002 | Nason et al. | |
| 6,402,859 B1 * | 6/2002 | Ishii | A61L 29/02 148/421 |
| 6,673,079 B1 | 1/2004 | Kane | |
| 6,678,562 B1 | 1/2004 | Tepper et al. | |
| 6,702,802 B1 | 3/2004 | Hancock et al. | |
| 6,752,808 B2 | 6/2004 | Schumacher | |
| 6,786,910 B2 | 9/2004 | Cohen et al. | |
| 6,835,207 B2 | 12/2004 | Zacouto et al. | |
| 7,018,402 B2 | 3/2006 | Vito et al. | |
| 8,048,028 B2 | 11/2011 | Horn et al. | |
| 8,177,743 B2 | 5/2012 | Lennox | |
| 8,268,009 B2 | 9/2012 | Teitelbaum et al. | |
| 8,388,674 B2 | 3/2013 | Sandhu et al. | |
| 2002/0095120 A1 | 7/2002 | Larsen et al. | |
| 2004/0087827 A1 | 5/2004 | Lubock | |
| 2005/0010191 A1 | 1/2005 | Skinner et al. | |
| 2006/0052753 A1 | 3/2006 | Mansouri | |
| 2006/0069403 A1 | 3/2006 | Shalon et al. | |
| 2006/0079897 A1 | 4/2006 | Harrison et al. | |
| 2006/0189899 A1 | 8/2006 | Flaherty et al. | |
| 2007/0119165 A1 | 5/2007 | Yson et al. | |
| 2007/0219466 A1 | 9/2007 | Tremulis et al. | |
| 2008/0200839 A1 | 8/2008 | Bunch et al. | |
| 2010/0114017 A1 * | 5/2010 | Lenker | A61B 17/12118 604/96.01 |
| 2011/0152683 A1 | 6/2011 | Gerrans et al. | |
| 2011/0224625 A1 | 9/2011 | Flickinger et al. | |
| 2011/0295234 A1 | 12/2011 | Eaton | |
| 2012/0016342 A1 | 1/2012 | Brecker | |
| 2012/0059401 A1 | 3/2012 | Konstantino et al. | |
| 2012/0083820 A1 | 4/2012 | Carman et al. | |
| 2012/0095385 A1 | 4/2012 | Dominguez et al. | |
| 2012/0289982 A1 | 11/2012 | Gunday et al. | |
| 2013/0030425 A1 | 1/2013 | Stewart et al. | |
| 2013/0041244 A1 * | 2/2013 | Woias | A61B 5/0215 600/381 |
| 2013/0066155 A1 | 3/2013 | Keating et al. | |
| 2013/0116655 A1 | 5/2013 | Bacino et al. | |
| 2013/0253426 A1 | 9/2013 | Campbell et al. | |
| 2013/0289498 A1 * | 10/2013 | Bosma | A61M 25/0009 604/265 |
| 2014/0066898 A1 | 3/2014 | Cully et al. | |
| 2014/0088362 A1 | 3/2014 | Terliuc et al. | |
| 2015/0081006 A1 | 3/2015 | Chuter et al. | |

FOREIGN PATENT DOCUMENTS

| | | |
|---|---|---|
| SU | 1814906 A1 | 5/1993 |
| WO | 9114395 A1 | 10/1991 |
| WO | 2010/124126 A2 | 10/2010 |
| WO | 2014028922 A2 | 2/2014 |

OTHER PUBLICATIONS

International Search Report and Written Opinion regarding PCT/US2015/031956 dated Aug. 28, 2015.
Early Commercial Assessment for Discussion, May 7, 2014, "Organ Repair, Hemostasis, and In Vivo Bonding of Medical Devices by Aqueous Solutions of Nanoparticles," Meddahi-Pellé, Ann et al.
Journal of Pediatric Surgery, vol. 38, No. 6, pp. 881-885, Jun. 2003, "Serial Transverse Enteroplasty for Short Bowel Syndrome: A Case Report," Heung Bae Kim et al.
American Pediatric Surgical Association, pp. 1085-1090, May 2002, "Longitudinal Mechanical Tension Induces Growth in the Small Bowel of Juvenile Rats", S. D. Safford et al.
Journal of The Royal Society of Medicine, vol. 90, pp. 429-432, Aug. 1997, "Longitudinal Intestinal Lengthening and Tailoring: Results in 20 Children", A. Bianchi M.D. et al.
Journal of The Royal Society of Medicine, vol. 77, Supplement No. 3, pp. 35-41, 1984, "Intestinal Lengthening: An Experimental and Clinical Review", A. Bianchi M.D. et al.
Scandinavian Journal of Gastroenterology, pp. 48-54, 2001, "Effect of High-Dose Growth Hormone and Glutamine on Body Composition, Urine Creatinine Excretion, Fatty Acid Absorption, and Essential Fatty Acids Status in Short Bowel Patients", P. B. Jeppesen et al.
The Endocrine Society, vol. 138, No. 11, pp. 4837-4843, 1997, "Circulating and Tissue Forms of the Intestinal Growth Factor, Glucagon-Like Peptide-2", Patricia L. Brubaker et al.
Journal of Pediatric Surgery, vol. 36, No. 1, pp. 178-183, Jan. 2001, "Analysis of Patients With Longitudinal Intestinal Lengthening Procedure Referred for Intestinal Transplantation", Javier Bueno et al.
Journal of Surgical Research 77, Article No. JR985362, pp. 17-22, 1998, "The EGF/EGF-Receptor Axis Modulates Enterocyte Apoptosis During Intestinal Adaption", Michael A. Helmrath, M.D. et al.
The Journal of Immunology, vol. 172, pp. 4151-4158, 2004, "Intestinal Intraepithelial Lymphocyte ??-T Cell-Derived Keratinocyte Growth Factor Modulates Epithelial Growth in the Mouse", Hua Yang et al.

(56) References Cited

OTHER PUBLICATIONS

The American Gastroenterological Association, vol. 130, pp. 117-121, 2006, "Novel Agents in the Treatment of Intestinal Failure: Humoral Factors", Hua Yang et al.
Journal of Pediatric Surgery, vol. 41, pp. 763-767, 2006 "Distension Enterogenesis: Increasing the Size and Function of Small Intestine," Devin P. Puapong et al.
Journal of Surgical Research, vol. 170, No. 1, Sep. 2011, Association for Academic Surgery, "Distraction Induced Enterogenesis: A Unique Mouse Model Using Polyethylene Glycol," Manabu Okawada, M.D. et al.
Annals of Surgery, vol. 255, No. 2, pp. 302-310, Feb. 2012, "Distraction-Induced Intestinal Enterogenesis—Preservation of Intestinal Function and Lenghthening after Reimplantation into Normal Jejunum," Hiroyuki Koga, M.D. et al.
Journal of Pediatric Surgery, vol. 39, No. 12, pp. 1823-1827, Dec. 2004, "Enterogenesis by Mechanical Lengthening: Morphology and Function of the Lenthened Small Intestine," Jinyoung Park et al.
Surgery Journal, vol. 140, No. 2, pp. 212-220, 2006, "Enterogenesis in a Clinically Feasible Model of Mechanical Small-Bowel Lengthening," Ariel U. Spencer, M.D. et al.
Journal of Surgical Research, pp. 1-6, Apr. 2011, "Flow Through a Mechanical Distraction Enterogenesis Device: A Pilot Test," Eiichi A. Miyasaka, M.D. et al.
International Conference on Adaptive Structures and Technologies, Oct. 2011, "Design and In Vivo Validation of an Implantable SMA Driven Bowel Extender for Correcting Short Bowel Syndrome," Brent Utter et al.
Proceedings of SPIE, vol. 6173, 617309, 2006, "Mechanical Extension Implants for Short-Bowel Syndrome," Jonathan Luntz et al.
Journal of Pediatric Surgery, vol. 46, pp. 2321-2326, 2011, "Restoration of Mechanically Lengthened Jejunum into Intestinal Continuity in Rats," Rebecca Stark et al.
Digestion, vol. 58, pp. 240-248, 1997, "Small Bowel Lengthening by Mechanical Distraction," Hartmut Printz, M.D. et al.
Proceedings of ASME 2010 Conference on SMASIS2010-3895, 2010, "Design of an SMA Actuated Mechanotransductive Implant for Correcting Short Bowel Syndrome," Brent Utter et al.
Journal of Pediatric Surgery, vol. 41, pp. 2019-2022, 2006, "Sustainability of Mechanically Lengthened Bowel in Rats," Paul C.Y. Chang et al.
Journal of Pediatric Surgery, vol. 45, pp. 1575-1580, 2010, "The Feasibility of Using an Endoluminal Device for Intestinal Lengthening," Shant Shekherdimian et al.
Journal of Surgical Research, vol. 163, No. 2, pp. 169-175, 2010, "Association for Academic Surgery, Application of Distractive Forces to the Small Intestine: Defining Safe Limits," Eiichi A. Miyasaka, M.D. et al.
ECCOMAS Conference on Smart Structures and Materials, SMART2013, Jun. 2013, "A Shape Memory Alloy Driven and Instrumented Bowel Extending Device for Investigating the Mechanotransduction Based Approach to Correcting Short Bowel Syndrome," Brent Utter et al.
Journal of Pediatric Surgery, vol. 47, pp. 136-141, 2012, "Development of an Endoluminal Intestinal Lengthening Capsule," Rebecca Stark et al.
Demehri, Farokh R. et al., "Development of an Endoluminal Intestinal Attachment for a Clinically Applicable Intestinal Lengthening Device," APSA2015 46th Annual Meeting Final Program, May 3, 2015, pp. 216-217.
Demehri, Farokh R. et al., "A Novel Therapy for Short Bowel Syndrome: Bowel Lengthening Device," Lifeline Letter, vol. XXXV, No. 6, Nov. 2014, pp. 1, 6, 7.
Utter, Brent Allen, "Technological Approaches for Investigating Mechanotransductive Enterogenesis: A Dissertation Submitted in Partial Fulfillment of the Requirements for the Degree of Doctor of Philosophy (Mechanical Engineering)," The University of Michigan, Oct. 13, 2014, pp. 1-242.
Extended European Search Report dated Dec. 6, 2017 regarding corresponding European Application No. 15795829.9, 13 pages.
Supplementary Partial European Search Report dated Aug. 20, 2018 regarding corresponding European Application No. 16740895.4, 12 pages.

* cited by examiner

Tensioned Bowel Segment

Grown Bowel

*Fig-4E*

Repeat

ATRAUMATIC TIP GEOMETRY FOR INDWELLING DEVICES

CROSS-REFERENCE TO RELATED APPLICATIONS

This application is a continuation-in-part of U.S. patent application Ser. No. 14/718,175 filed on May 21, 2015. This application claims the benefit of U.S. Provisional Application No. 62/106,859, filed on Jan. 23, 2015. The entire disclosure of the above applications is incorporated herein by reference

GOVERNMENT INTEREST

This invention was made with government support under FD003787 awarded by the Food and Drug Administration. The government has certain rights in the invention.

FIELD

The present disclosure relates to indwelling devices and, more particularly, relates to an atraumatic tip geometry having tapering stiffness allowing for atraumatic placement of an indwelling device inserted in biological tubular structures.

BACKGROUND AND SUMMARY

This section provides background information related to the present disclosure which is not necessarily prior art. This section provides a general summary of the disclosure, and is not a comprehensive disclosure of its full scope or all of its features.

Distraction enterogenesis (DE) may provide a novel therapy for short bowel syndrome (SBS). Previously described methods have relied upon isolated intestinal segments or transmural fixation due to ineffective endoluminal attachment. The present teachings provide a novel approach using geometric coupling between a tapering device and the mesenteric curvature to allow trans-stomal distraction enterogenesis.

A catheter device with tapering stiffness was developed, consisting of, in some embodiments, a stiff catheter with a taper to a flexible latex tip to prevent perforation. Yorkshire pigs underwent creation of a jejunal Roux limb with device placed via jejunostomy. Intestinal attachment was achieved without substantial reduction in bowel perfusion as measured by laser Doppler. An external clamp was secured at the stoma to provide external fixation of the device. The catheter was advanced 1 cm/day for either 7 or 14 days before explant.

After 7 days, the distracted segment achieved a mean±SD increase in length of 37±6% versus fed, nondistracted bowel, corresponding to an absolute gain of 10.6±1.7 cm (1.5 cm/day). After 14 days, the Roux limb achieved an 80±2% increase in length versus fed control bowel, corresponding to an absolute gain of 16.8±3.0 cm (1.2 cm/day). No perforation or stoma-related complication occurred.

More generally, the principles of the present teachings provide an indwelling device for insertion in a biological tubular structure comprising an elongated device having a body and opposing ends. The body has a bending stiffness transverse to a longitudinal axis that is greater than a stiffness of the biological tubular structure. An atraumatic tip member, having a proximal end and a distal end, extends from the end of the elongated device. The proximal end has a first bending stiffness transverse to a longitudinal axis and the distal end has a second bending stiffness transverse to the longitudinal axis, wherein the second bending stiffness being less than the first bending stiffness.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Introduction

Short bowel syndrome (SBS), where loss of small bowel length results in insufficient nutrient absorptive capacity for growth and development, is the most common cause of pediatric intestinal failure. Survival among patients with SBS is predicted by the length of the residual small bowel, making the restoration of intestinal length an attractive strategy. Operative lengthening procedures have been developed but carry the risk of complications (e.g., infection, perforation, bleeding, and obstruction) and are limited to patients with favorable anatomy (e.g., dilated small bowel). Small bowel transplantation has been used less frequently in recent years, partially because of less-than-optimal outcomes, with graft failure and rejection approaching 60% at 5 years. Therefore, therapy for SBS consists primarily of supportive therapy with supplemental or total parenteral nutrition, which carries risks of hepatic dysfunction, metabolic derangement, and sepsis.

Distraction enterogenesis may provide a therapeutic option for the treatment of SBS patients who otherwise face little chance of achieving enteral autonomy. Distraction enterogenesis is the use of mechanical force to induce small bowel lengthening and has been shown in animal models to produce durable increases in length with preservation of intestinal function. Increased intestinal length is accompanied by mesenteric neovascularization, muscular hypertrophy, increased mucosal surface area, and increased epithelial cell proliferation.

Although distraction enterogenesis has shown promise in animal models, it has yet to become a clinically applicable strategy. Previous methods of distraction enterogenesis have been limited by the use of blind-ending intestinal segments or transmural sutures to allow attachment of the device, which is necessary for transmission of mechanical force to the intestinal wall. These methods of attachment require an implant operation to create the blind-ending segments or to place sutures, followed by a second explant operation to restore continuity. The restoration of intestinal continuity may result in the loss of gained intestinal length—up to 39%—because of the need for creation of a new anastomosis. In addition, patients with SBS have been shown to mount a postoperative inflammatory response, making multiple intestinal operations a high-risk proposition for such patients.

According to the present teachings, in some embodiments, a device and method for distraction enterogenesis is provided that employs a fully endoluminal intestinal lengthening device that exerts a lengthening force on an organ. As should be appreciated from the discussion, the principles of the present teachings are equally applicable to any device that is inserted and/or indwelling within a soft tubular organ or similar bodily feature of a human or animal. By way of non-limiting example, the present teachings are particularly well adapted for use in a bowel (i.e. large bowel), esophagus, artery, vein, and the like, and thus the present discussion will be particularly directed thereto.

The present teachings obviates the need for surgical placement of the device beyond the creation of an intestinal stoma (gastrostomy or enterostomy), which many patients with SBS already have because of their underlying disease. The use of a novel catheter with progressive reduction in stiffness allows endoluminal small bowel fixation. The geometric intestinal attachment allows distraction and intestinal lengthening via a jejunostomy. Safety and efficacy of this approach are demonstrated in a well-established swine model.

Device Design

According to the principles of the present teachings as illustrated in the figures, a device 10, for example, is provided having an atraumatic tip 12 extending from at least one end thereof. The structure of the atraumatic tip 12 will be described in detail herein. Device 10 can be any device suitable for insertion and/or indwelling within a tubular organ or structure of a human and/or animal (e.g. a biological tubular structure, such as a bowel (i.e. large bowel), esophagus, artery, vein, and the like). Although it should be appreciated that the principles of the present teachings will define advantages in a wide range of applications, the teachings will be described in connection with an exemplary reciprocating linear hydraulic device 10 that exerts a lengthening force on an organ.

Elongation Device

In some embodiments, device 10 can comprise an elongation system 200. In some embodiments, elongation system 200 can be a mechanotransduction enterogenesis device for use in lengthening soft tissue (e.g. bowel). It should be understood, however, that the present disclosure is not to be regarded as requiring an elongation system or other component unless specifically claimed. In some embodiments, elongation system 200 can comprise an elongated member or device 202 having a body with opposing ends 204, 206 (i.e. distal and proximal ends). The body can be rigid in a direction transverse to a longitudinal axis (i.e. a bending stiffness) of the body. In some embodiments, the body can define a bending stiffness that is greater than the stiffness of the biological tubular structure in which it is inserted and/or indwelling. The body can be generally tubular or define any other shape complementary to the biological tubular structure. In some embodiments, one or more of the opposing ends 204, 206 can comprise a fenestrated attachment system 220, which will be described in greater detail herein. Internal to and/or between opposing ends 204, 206, as illustrated in FIGS. 4A-4E, elongation system 200 can comprise an extending or actuation mechanism 208 that is operable to longitudinally drive elongation system 200 between an extended position and a retracted position. In the extended position (see FIGS. 2 and 4C), the opposing ends 204, 206 and the associated fenestrated attachment system 220 define a spaced-apart orientation. In the retracted position (see FIGS. 1 and 4B), the opposing ends 204, 206 and the associated fenestrated attachment system 220 define a spaced-together orientation. In this way, in the retracted position, ends 204, 206 are in their narrowest configuration and, in the extended position, ends 204, 206 are in their widest configuration. As will become apparent, if both fenestrated attachment systems 220 are engaged with the interior surface 102 of the hollow member 100, movement between the retracted position and the extended position can result in application of a tensile force to the hollow member 100 proportional to the force exerted by extending mechanism 208. Likewise, if only one fenestrated attachment system 220 is engaged with the interior surface 102 of the associated hollow member, movement between the retracted position and the extended position can result in application of a translational force.

In some embodiments, extending mechanism 208 can comprise a reciprocating linear hydraulic actuator. However, it should be understood that a wide variety of drive actuation devices can be used in connection with extending mechanism 208, including hydraulic, pneumatic, push-cable driven, screw-driven, SMA wire, SMA helical spring, SMA-driven ratchet, thermal expansion/phase change actuator driven, electromagnetic actuator (solenoid, linear stepper motor, rotary screw drive motor). For additional detail relating to these actuation systems, reference should be made to commonly-owned U.S. Pat. Nos. 7,722,560 and 8,268,009, which are hereby incorporated and made a part of the present application.

In some embodiments, extending mechanism 208, when configured as a reciprocating linear hydraulic actuator, is based on a "payout" approach. By repeating the operation cycle, the length of tissue growth induced is limited only by the number of times extending mechanism 208 is cycled rather than the stroke of extending mechanism 208. In some embodiments, extending mechanism 208 can be concealed and/or protected using a sheath 210, such as a thin silicone sheath, to protect extending mechanism 208 from associated environmental contaminants and to facilitate operation. For example, when the device is retracted, the thin silicone sheath prevents the bowel from pleating between the attachments, promoting the repositioning of bowel relative to the attachments.

Fenestrated Attachment System

Figure 5:
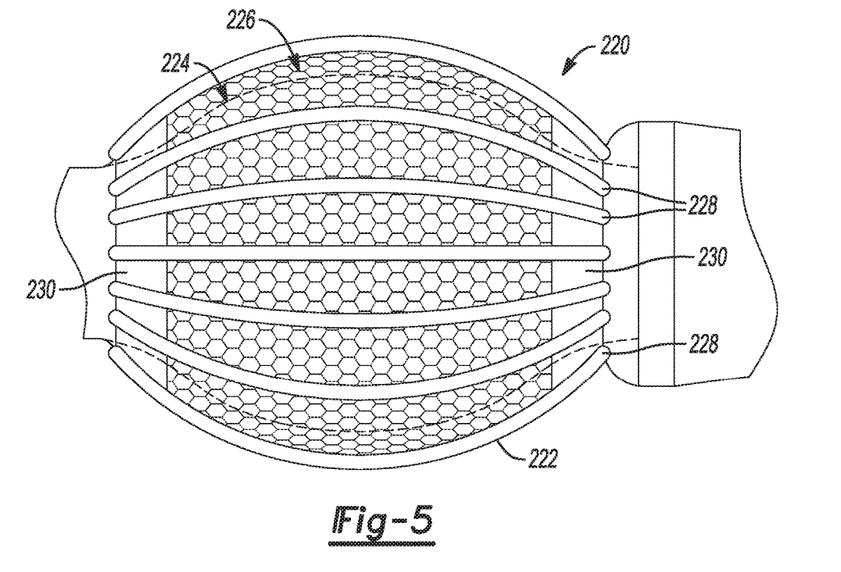
FIG. 5 is a side view illustrating the fenestrated decoupling device according to the principles of the present teachings.

In some embodiments, to facilitate the selective attachment and detachment of elongation system 200 from the bowel lumen or other hollow member 100, a fenestrated attachment system 220, such as an endoluminal balloon attachment mechanism, is provided that employs a fenestrated decoupling system 222 as illustrated in FIG. 5. The fenestrated attachment system 220 is placed within the bowel lumen or other hollow organ member 100 and is capable of radially expanding, thereby coupling with the inner luminal surface 102 of the bowel or other interior surface 102 of the hollow member 100, to allow transfer of longitudinal tensile loads to the bowel wall or hollow member 100 and/or permit translation therethrough.

In some embodiments, fenestrated attachment system 220 comprises an expanding device 224 (e.g. balloon) disposed on at least one end 204, 206. In some embodiments, expanding device 224 is enlargeable between a deflated position (first size position) and an inflated position (second size position), whereby the inflated position is sufficiently large to permit mechanical engagement with the interior surface 102 of the hollow member 100 (i.e. bowel lumen). It should be understood that in some embodiments, the size of the inflated position must be sufficiently large to further accommodate any resultant enlargement of the hollow member in response to application of the inflation force. Likewise, it should be understood that in some embodiments, the size of the deflated position must be sufficiently smaller to permit disengagement of fenestrated attachment system 220 from the interior surface 102 of hollow member 100, at least when used in conjunction with fenestrated decoupling system 222.

In some embodiments, fenestrated attachment system 220 further comprises a friction enhancement or texture 226. In some embodiments, friction enhancement 226 can comprise application of an abrasive texture generally surrounding expanding device 224 that is capable of expanding during inflation of expanding device 224 and retracting during deflation of expanding device 224. In some embodiments, it has been found that an open-cell matrix, such as a 3M, Scotch-Brite Dobie, is useful. In some embodiments, friction enhancement 226 can comprise a fabric material structure surrounding expanding device 224. The fabric material structure can include one or more fibers knitted into a series of interlocked loops such that the knitted fabric can expand and contract along with expanding device 224. The loops can engage the interior surface 102 of the hollow member 100. In some embodiments, the fibers can include a flat ribbon such that the edges of the flat ribbon engage with the interior surface of the hollow member. In some embodiments, the friction enhancement 226 can include a plurality of bristles fixed to expanding device 224 engageable with the interior surface of the hollow member. In some embodiments, the friction enhancement 226 can include a plurality of loops fixed to the expanding member which engage the interior surface of the hollow member. Moreover, in some embodiments, the friction enhancement 226 comprises a plurality of scales, suction cups, and/or ridges fixed to the expanding device 224 which engage with the interior surface of the hollow member.

However, it was found that in some applications, friction enhancement 226 may not reliably disengage from interior surface 102 of hollow member 100 even after expanding device 224 is deflated and friction enhancement 226 is in the retracted position. Failure to disengage from interior surface 102 may inhibit further insertion, removal, and/or purposeful repositioning of the device. Accordingly, fenestrated decoupling system 222 can be employed about friction enhancement 226 to encourage disengagement of friction enhancement 226 from interior surface 102 upon deflation of expanding device 224. In some embodiments, fenestrated decoupling system 222 can comprise a plurality of bands 228 being disposed longitudinally along friction enhancement 226 at radial positions radially thereabout. In some embodiments, the plurality of bands 228 are comprises of elastic bands, which can be made of a monofilament material. The plurality of bands 228 can be retained by a pair of ring members 230 disposed at opposing sides of fenestrated attachment system 220 that permit the plurality of bands 228 to pass there over and be captured and retained within fenestrated attachment system 220.

During operation, in some embodiments, fenestrated decoupling system 222 is operable to expand to accommodate inflation of expanding device 224 and, by association, enlarge friction enhancement 226, thereby permitting friction enhancement 226 to engage the interior surface 102 of hollow member 100. Once friction enhancement 226 is operably engaged with interior surface 102, extending mechanism 208 of elongation system 200 can be actuated. Conversely, once actuation is complete, expanding device 224 can be deflated and, by association, retract friction enhancement 226. This permits friction enhancement 226 to retract. The plurality of bands 228 of fenestrated decoupling system 222 can similarly retract. Retraction of friction enhancement 226 to a size smaller than retraction of the plurality of bands 228 of fenestrated decoupling system 222 can permit the plurality of bands 228 to disengage interior surface 102 of hollow member 100 from friction enhancement 226, thereby permitting insertion, removal, and purposeful repositioning of the device.

In some embodiments, fenestrated decoupling system 222 can comprise a non-expanding device that is sufficiently fenestrated to permit expanding device 224 and friction enhancement 226 to extend through the fenestrated portions to a position exterior of fenestrated decoupling system 222 thereby engaging interior surface 102. Upon deflation of expanding device 224, expanding device 224 and friction enhancement 226 can collapse within a volume defined by fenestrated decoupling system 222, thereby disengaging from interior surface 102.

Atraumatic Tip

Figure 1:
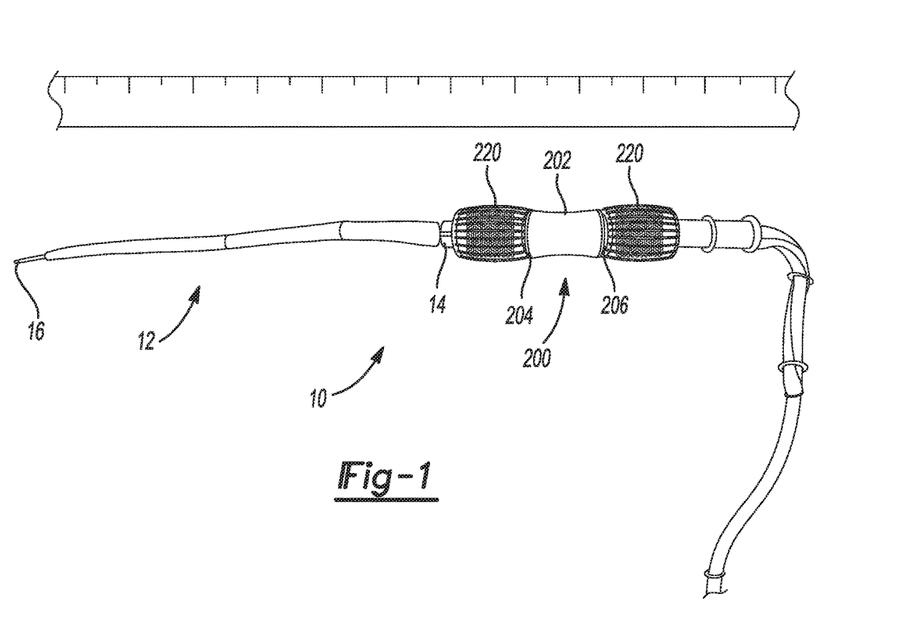
FIG. 1 is a perspective view of an indwelling device for distraction enterogenesis having an atraumatic tip geometry according to the principles of the present teachings in a first size position (e.g. deflated)
Figure 2:
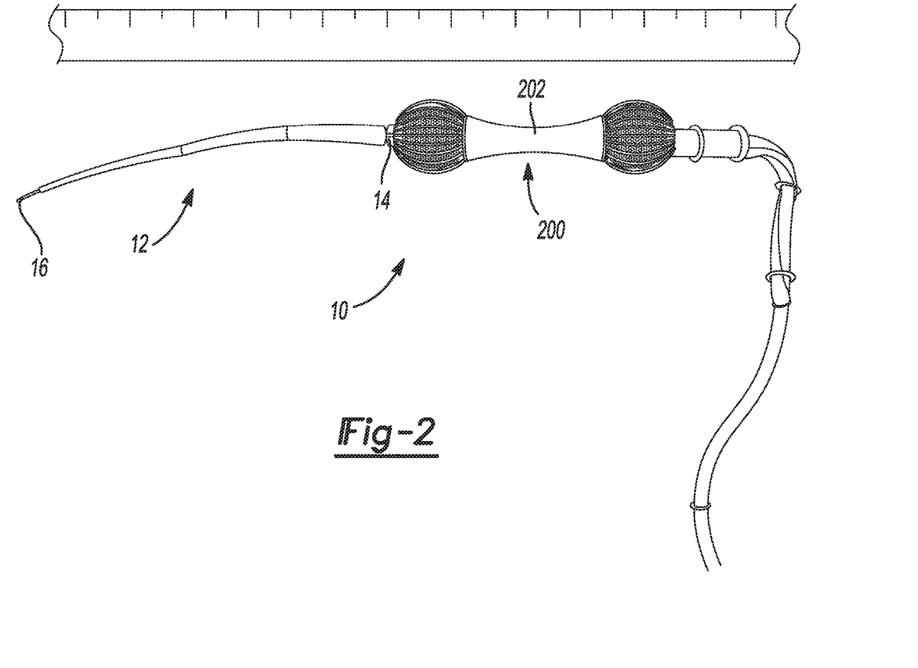
FIG. 2 is a perspective view of the indwelling device for distraction enterogenesis having the atraumatic tip geometry according to the principles of the present teachings in a second size position (e.g. inflated)
Figure 3:
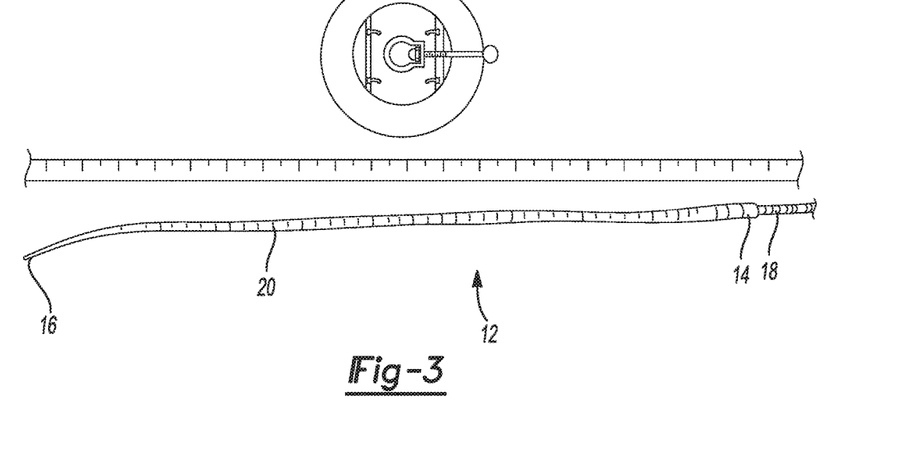
FIG. 3 is a perspective view of the atraumatic tip geometry according to some embodiments.
Figure 4A:
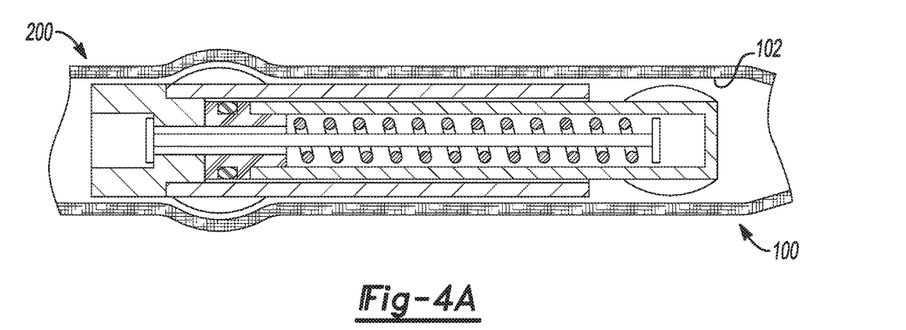
FIGS. 4A-4E illustrate a series of cross-sectional schematic views of actuation of an elongation system according to the principles of the present teachings.
Figure 4B:
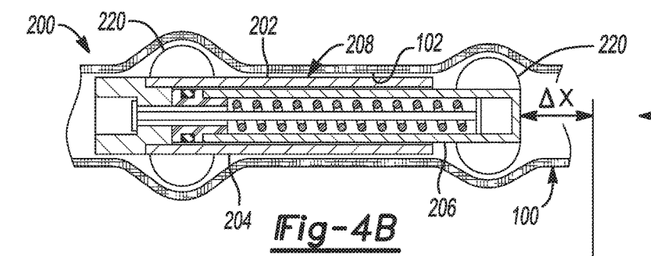
Figure 4C:
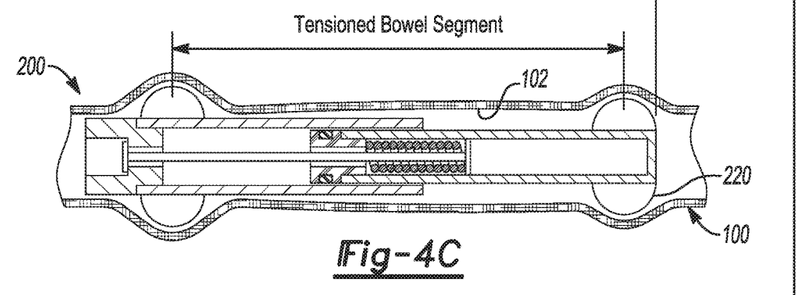
Figure 4D:
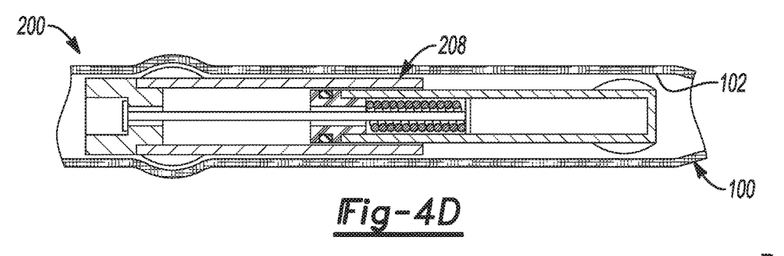
Figure 4E:
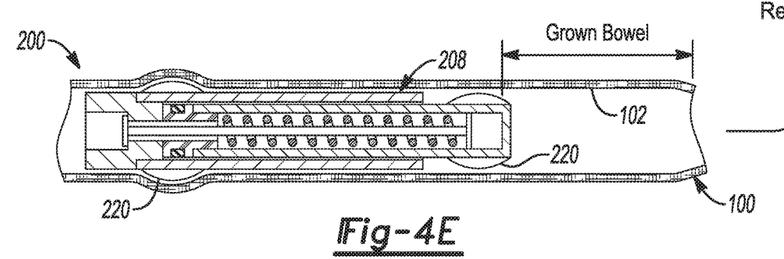

According to the principles of the present teachings, as illustrated in FIGS. 1-3, atraumatic tip 12 is employed to provide progressive tapering or reduction in the amount of stiffness along at least a portion of the length of the device 10. More particularly, the stiffness of a proximal end 14 of atraumatic tip 12 that is adjacent an end of elongation system 200 and/or fenestrated attachment system 220 is generally greater than a distal end 16 of atraumatic tip 12. In some embodiments, this stiffness reduction along the length of atraumatic tip 12 can be linear, exponential, or define a non-linear predetermined reduction. Atraumatic tip 12 can comprise one or more internal flexure members 18 and an optional covering or sheath 20 disposed about flexure members 18.

Figure 6:
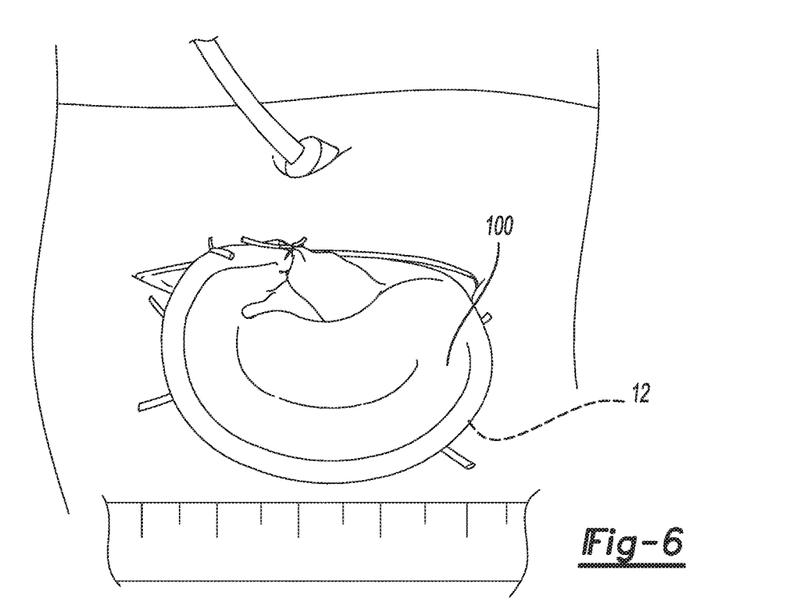
FIG. 6 illustrates the device inserted into a tubular organ where the gradual increase in stiffness with device insertion allows geometric coupling with the mesenteric curvature of the jejunal Roux limb.

By way of a non-limiting example, in some embodiments, atraumatic tip 12 can comprise a 3.26-mm diameter stranded cable serving as flexure member 18 (8 AWG; [American wire gauge]; Southwire, Carrollton, Ga.), consisting of 19 strands of 0.72-mm diameter copper wire. Each strand can be trimmed at 1-cm intervals to decrease progressively the total strand count approaching the distal end 16, thereby decreasing progressively the stiffness. The trimmed stranded cable can be inserted into a latex sheath or other covering 20 that is tapered gradually over a length of 33 cm from a 24-Fr base to an 8-Fr end. The internal flexure member 18 can end at a distance less than the length of the covering 20, such as about 14 cm proximal to the end of the latex sheath 20. The total length of atraumatic tip 12 can be about 80 cm. These materials and dimensions were chosen such that the most rigid end (i.e. proximal end 14) of the atraumatic tip 12 (the fully stranded 8 AWG wire) was stiff relative to the bowel (i.e., if advanced 'as-is' into the small intestine via the stoma, it would eventually lead to a perforation). The distal end 16 of atraumatic tip 12, by contrast, was selected such that it was more flexible than the bowel itself (i.e., when an 8-Fr latex catheter was advanced "as-is" in to the small intestine, it would conform to the intestinal curvature as illustrated in FIG. 6). We found that if the end of the device was stiff relative to the bowel, it would exert focal radial force on the intestinal wall, which over time with distraction would lead to ischemia/perforation.

In addition to a flexible end, a gradual transition in stiffness along the length of atraumatic tip 12 was found to be important. If stiffness of the device decreased abruptly at any point along the device, the intestine would drape acutely over this abrupt transition. This "tip-effect" resulted in a disproportionate amount of longitudinal distractive force being applied in a concentrated area of the bowel wall at that point of transition. In previous devices where such a tapered tip was not used, perforation occurred at the end of the device.

Figure 7:
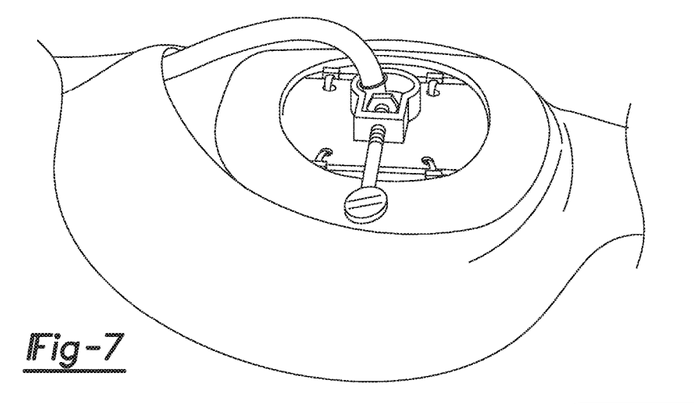
FIG. 7 illustrates a stoma clamp providing external fixation.

In some embodiments, to fixate device 10 to the abdominal wall and allow transmission of the applied force to the targeted area for small bowel lengthening, a clamp (FIG. 7) can be mounted on a 10-cm wide rubber base, which can be sutured to the abdominal wall at the stoma site. After each advancement of the device, this clamp can be applied to provide proximal fixation of the device at the level of the stoma.

Mechanical Characterization.

Figure 8:
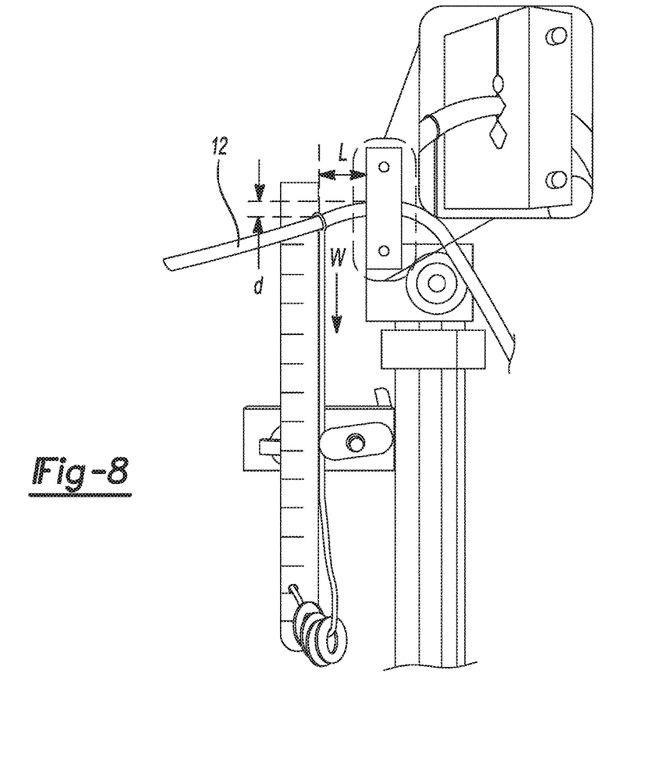
FIG. 8 illustrates a system for testing the mechanical characterization of the atraumatic tip geometry where weights (W) are hung from the atraumatic tip at a set distance (L) from a v-groove clamp at select points along the atraumatic tip, where the vertical deflection (d) is measured and used to compute the bending stiffness at that point along the tip.
Figure 9:
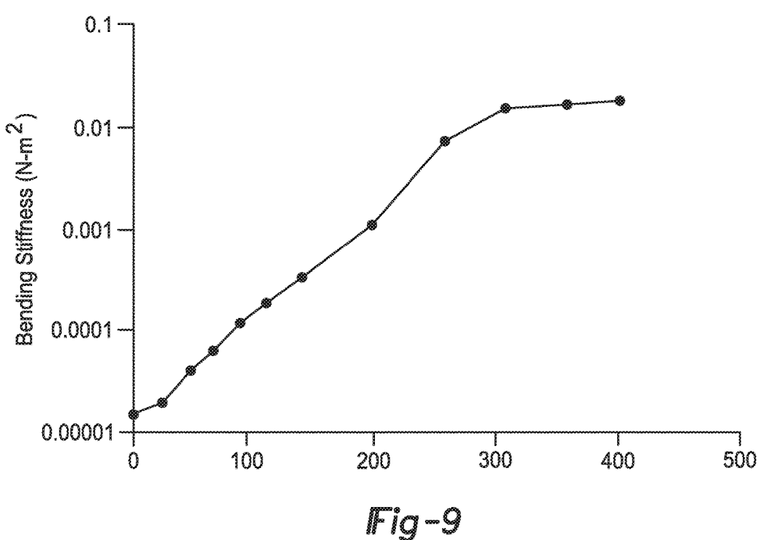
FIG. 9 is a graph illustrating the bending stiffness of the atraumatic tip at various distances from the distal end of the atraumatic tip.
Figure 10:
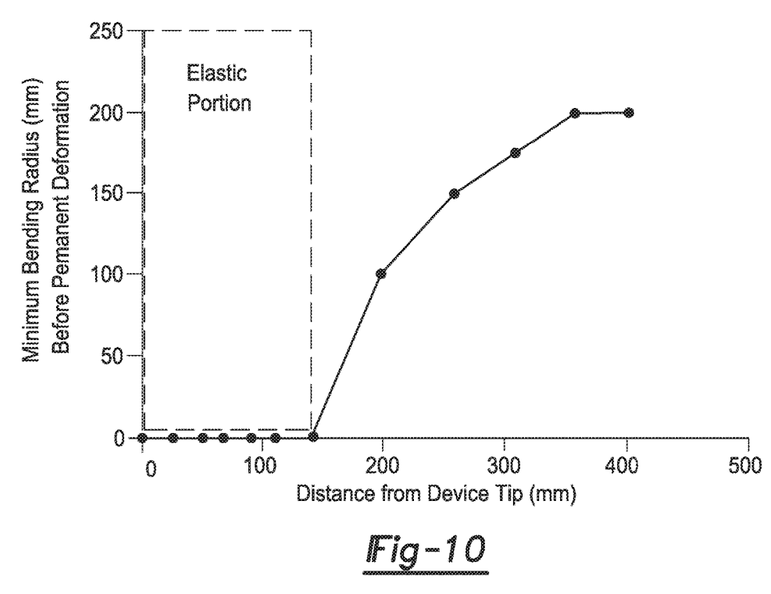
FIG. 10 is a graph illustrating the minimum bending radius of the atraumatic tip before permanent bending measured at select points along the portion of the atraumatic tip.

To quantify the mechanical characteristics of the device, the bending stiffness of atraumatic tip 12 was measured along the length of its tapered portion. Bending stiffness is defined as the ratio between an applied bending moment, measured in N-m (Newtonsmeter), and the resulting curvature (reciprocal of the radius of curvature, or 1/m) with resulting units of N-m2. Measurements of bending stiffness were performed by measuring the linear stiffness of a cantilevered section of atraumatic tip 12 (FIG. 8). The atraumatic tip 12 was fixed horizontally in a V-groove clamp at a specified point along its length, and a series of weights (varying between 0.186 g and 250 g) were hung from a thread tied at a set test length distance (ranging from 15 to 50 mm) from the clamp. The vertical deflection was measured as a function of load, where, according to classical linear beam theory, the bending stiffness is equal to one third times the test length cubed times the ratio between the applied load and the tip deflection. The resulting bending stiffness ranged from a maximum of $1.89 \times 10^{-2}$ $Nm^2$ at the proximal end of atraumatic tip 12 to $1.5 \times 10^{-5}$ $Nm^2$ at the distal end (FIG. 9).

Another important mechanical property of the device that needed to be quantified was the maximum curvature that could be applied before the catheter was bent permanently attributable to the malleability of the copper. The curvature was measured by bending atraumatic tip 12 to a radius of curvature (relative to a set of printed concentric circles of known radius) and releasing, decreasing the radius of curvature progressively until the device no longer sprang back to its original straight configuration. This test was repeated at varying positions along the malleable portion of atraumatic tip 12. The smallest radius that allowed complete spring-back (plotted as a function of position along the device; FIG. 2, C) varied from 200 mm at the proximal end of the device to 100 mm where the internal wire structure ended distally. This radius relates to the largest amount of bending moment atraumatic tip 12 can apply to the bowel before atraumatic tip 12 takes a permanent "pose," conforming to the bowel, after which the residual force on the bowel takes on a maximum at the value required to bend atraumatic tip 12 into that pose.

Animal Model.

Atraumatic tip 12 was tested using a swine model for distraction enterogenesis. Female Yorkshire pigs weighing 30-40 kg were used for each experiment (n=4) according to accepted protocols. Although the future clinical application is intended to be placed via a gastrostomy (or nasoenteric tube), the course of the porcine duodenum is far more tortuous than that of a human. Thus, atraumatic tip 12 was placed via a proximal jejunostomy. Through a midline laparotomy, a Roux limb was created 90 cm distal to the ligament of Treitz and the proximal end was brought out as a jejunostomy in the left abdomen. The jejunostomy was secured in 3 layers at the skin, anterior fascia, and posterior fascia to prevent stoma retraction during distraction. An end-to-side anastomosis was created to form a Roux-en-Y jejuno-jejunostomy to restore intestinal continuity. The mesenteric defect was closed to prevent internal hernia. The clamp mount was sutured circumferentially to the abdominal wall at the stoma site. Device 10 was inserted via the stoma into the Roux limb, advancing atraumatic tip 12 first.

As the first mesenteric curve of the jejunal limb was encountered, atraumatic tip 12 of device 10 navigated this curve without bowel distortion. With continued advancement of the progressively stiffer device, however, a point was reached where atraumatic tip 12 was no longer flexible enough to navigate the mesenteric curvature, thus geometric fixation was achieved. Atraumatic tip 12 was clamped at this depth. Silastic markers (vessel loops) were placed along the antimesenteric border of the Roux limb at 3-cm intervals. These markers allowed for accurate measurement of gain or loss of intestinal length at harvest. A 12-cm segment was selected 10 cm distal to the jejuno-jejunostomy to serve as a fed control and was marked similarly at 3-cm intervals, which allowed paired analysis of lengthening between the distracted and fed control segment from each animal. Separate control sham operations were not performed. The abdomen was then closed in standard fashion. All animals were fed a regular solid diet beginning on the first postoperative day until device explant.

Device Advancement.

After a 24-hour recovery period, atraumatic tip 12 was advanced 1 cm/day by unclamping the stoma clamp to release the catheter, manually advancing the catheter 1 cm, and reapplying the stoma clamp.

Morphology Assessment.

At the end of the implant period, relaparotomy was performed. Device 10 was removed from the jejunostomy. Intervals between antimesenteric silastic markers were measured along the Roux limb and the control segment. The Roux limb was inspected grossly for evidence of mucosal damage or perforation. Full-thickness samples of the Roux limb at the contact areas with the device were resected and fixed in 10% formalin overnight. Samples were embedded in paraffin and stained with hematoxylin and eosin for histologic examination. Slides were visualized using a Nikon A-1 confocal microscope and assessed qualitatively for evidence of mucosal compromise, manifested as villus loss, mucosal sloughing, or changes in the submucosa or muscularis propria.

Tissue Perfusion Assessment.

To characterize the optimal initial tension to apply, visual and laser Doppler assessment of tissue perfusion was performed at each implant. After device insertion into the jejunal Roux limb and advancement until the depth of geometric fixation, the device was advanced further to create longitudinal bowel tension until occlusion of vessels along the antimesenteric bowel wall along the first mesenteric curve was observed. The device was then retracted until vessel reconstitution was observed, and the clamp was applied at this depth. This established the initial insertion tension.

Blood flow to the antimesenteric bowel wall was measured using a Lisca PIM II Laser Doppler Perfusion Imager (Perimed AB, Stockholm, Sweden), placed 10 cm above the antimesenteric surface of the first mesenteric curve along the jejunal Roux limb. Perfusion patterns were analyzed using LDPIwin 2.3 software (Perimed AB) as described previously, using triplicate measurements of a 1-cm2 tissue plane. Sequential measurements were taken at the same site with the device removed and with the device clamped at the initial insertion tension to quantify changes in tissue perfusion with distraction.

Analysis.

All lengthening measurements were made along the experimental Roux limb relative to a fed control segment. This approach allowed correction for the confounding effects of postlaparotomy inflammatory changes on bowel length. A paired t test was used to compare results from distracted and control segments from matched animals. Results were expressed as mean±SD unless otherwise specified.

Results

Lengthening.

Figure 11:
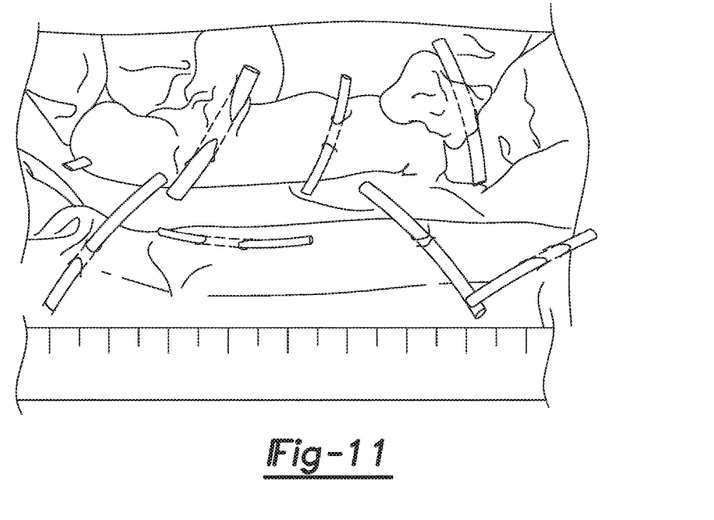
FIG. 11 illustrates silastic markers initially placed 3 cm apart demonstrating a significant increase in spacing after 7 days of distraction, wherein the distracted segment (arrow) and fed control (triangle) are shown without tension, with the device removed.
Figure 12:
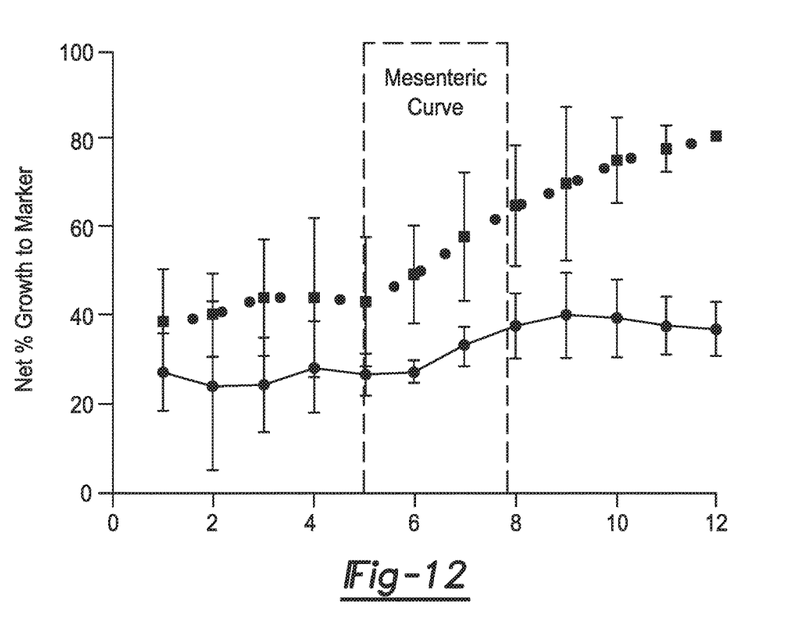
FIG. 12 is a graph illustrating the net percentage of growth versus marker number from the stoma to each marker (relative to fed control), with the region of geometric fixation (the first mesenteric curve of the jejunal Roux limb) indicated.

After 7 days, the distracted segment (measured after device removal) achieved a significant increase in length versus the fed, nondistracted bowel, without evidence of ischemia or perforation (see FIG. 11). Bowel lengthening was noted from the stoma to the end of the device, which was initially placed to marker 12 (i.e., initially 3-cm intervals, for a total of 36 cm deep to the stoma). The distance between markers along the distracted segment increased relative to the spacing of markers on the fed control segment. The cumulative percent net lengthening of the bowel in contact with the device relative to fed control was 37±6% after 7 days, and 80±2% after 14 days of distraction (see FIG. 12). Interestingly, although lengthening was seen throughout the distracted segment, the rate of lengthening increased sharply in the region of geometric attachment (the mesenteric curve). This rate increase was most notable after 14 days, where lengthening increased from 40% between markers 1 and 6 to 80% after marker 9. This change in lengthening efficacy may be the result to additional distractive forces being applied in the region of the mesenteric curve, where the longitudinal distraction of the device is coupled with radial force applied by displaced elastic catheter on the bowel wall.

Figure 13:
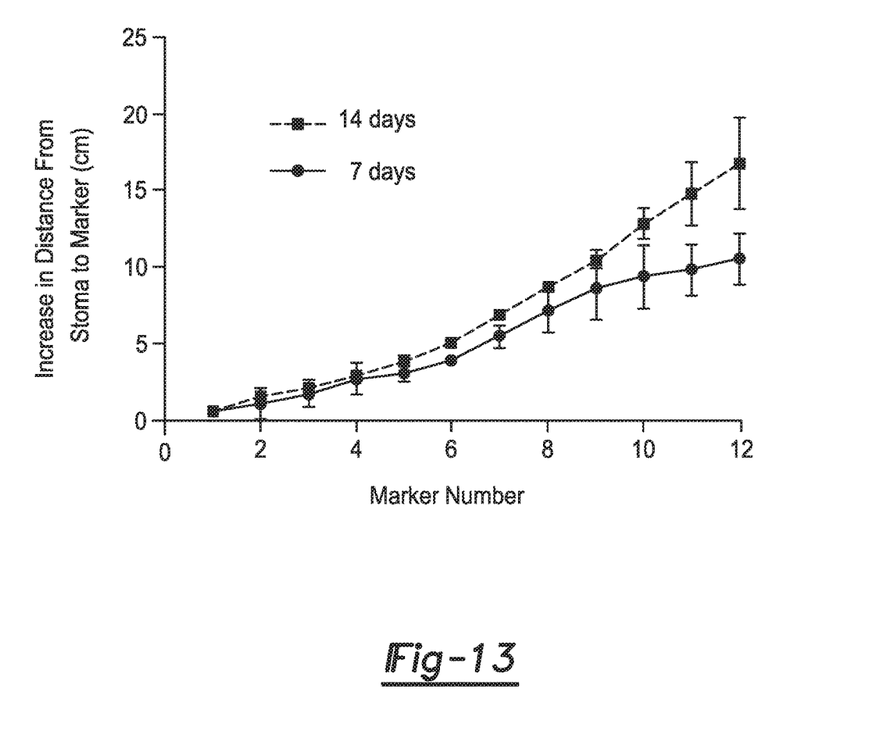
FIG. 13 is a graph illustrating the increase in distance from the stoma to each marker for the distracted segment relative to fed control.

The net gain in length was dependent on the length of bowel with which the device interacted. The cumulative distance from the stoma to each bowel marker along the distracted segment was measured and compared to a group of control segment marker intervals at explant, extrapolated over the same number of markers (see FIG. 13). The gain in length of the entire distracted segment relative to the fed control segment was 10.6±1.7 cm after 7 days, corresponding to an average lengthening rate of 1.5±0.2 cm/day. Doubling the duration of distraction to 14 days resulted in additional lengthening, with a net gain of 16.8±3.0 cm, and a slight decrease in daily gain to 1.2±0.2 cm/day. Interestingly, the rate of lengthening consistently exceeded the 1.0 cm/day advancement of the device. This change in length is consistent with prior methods of distraction enterogenesis, where bowel lengthening exceeded device expansion.

Device Safety.

No device-related perforation, bowel obstruction, or anastomotic complication occurred. Mucosa at device contact areas remained intact without ulceration. Histologic examination of the device contact areas revealed villus blunting with preservation of mucosal integrity as well as intact submucosa and muscularis propria. No serosal or mesenteric damage occurred. Peristomal skin remained intact, and no stomal retraction occurred.

Laser Doppler measurements showed no significant decrease in tissue perfusion at the antimesenteric aspect of the geometric attachment site (0.95±0.37 perfusion units (PU) vs 1.03±0.49 PU; bowel at-rest vs device tension applied; P=0.14). Laser Doppler measurements were repeated at explant, confirming no compromise in perfusion after chronic implant (0.09±0.23 PU vs 0.05±0.13 PU; P=0.07). PU is a dimensionless unit used for laser Doppler measurement. Environment-specific calibration prevents comparison of measurements at implant and explant.

This device used continuous distraction via daily advancement into the abdominal cavity. At explant of the 14 day implant group, the mesenteric curve of the distracted bowel was noted to abut the contralateral abdominal wall. Further device advancement was thus constrained by abdominal domain. No compression of surrounding organs was noted.

Discussion

Clinically applicable distraction enterogenesis requires maximizing bowel length gain while minimizing the morbidity of the distraction therapy. A fully endoluminal device may achieve this goal by allowing distraction without multiple operations. The present teachings demonstrate a method of and apparatus for endoluminal distraction enterogenesis using an indwelling, semirigid device with an atraumatic geometry of the end of the device. This strategy provides an effective method of intestinal attachment via geometric coupling of the device and mesenteric curvature. In addition, this geometry may improve the safety profile of any endoluminal device that is stiff relative to the bowel. Because the small intestine is nonlinear in orientation with the mesentery tethering the bowel in a curved course, an endoluminal device must conform to this curvilinear shape.

Devices that are stiff relative to the bowel, therefore, exert outward radial force on the small bowel and its mesentery (unless constructed to exactly match the bowel radius of curvature). At the end of a semirigid device, the bowel bends sharply over the device tip. This bending may create a focal point of radial force on the bowel, potentially inducing focal bowel ischemia and perforation. This phenomenon has been noted in a catheter-based endoluminal distraction enterogenesis device previously, and it may explain reports of delayed perforation from the ends of enteric feeding tubes. The gradual taper in stiffness of this device allowed for the catheter to exert progressively less radial force on the antimesenteric bowel wall as it approached the end of the device, preventing a sharp bend in the bowel over the end of the device, thereby decreasing the risk of perforation.

This method of distraction enterogenesis required an enterostomy for device insertion. Trans-stomal distraction enterogenesis has been described, although this technique relied on end-abutment of a stiff device on a surgically created intestinal blind end. Although such anatomy is not encountered frequently clinically, enterostomies and/or mucus fistulae often are present in patients with SBS. Trans-stomal distraction enterogenesis using geometric attachment may be a viable method of increasing residual bowel length in these patients. For example, such a device may be placed for a course of distraction therapy before takedown of the enterostomy in a patient who has undergone massive bowel resection and is at risk of SBS. This approach may allow the reversal of disuse atrophy if used via a mucous fistula, may induce substantial gain of length before takedown of the enterostomy with reanastomosis, and would not require additional operative maneuvers.

This device achieved lengthening rates that compared favorably to serial transverse enteroplasty (STEP) outcomes. Seven days of distraction produced 37±6% lengthening versus nondistracted fed bowel. This is similar to the current standard of care for patients with medically refractory SBS, the primary STEP procedure, which has been reported to produce a 22-43% increase in bowel length. It is important to note, however, that STEP results are measured at a single operative setting, while distraction enterogenesis requires interval measurement of lengthening after a set distraction period. In addition, lengthening via distraction occurs only in the length of intestine that contacts the device, whereas enteroplasty may be employed throughout the remaining bowel.

Importantly, this study demonstrated that prolonging distraction therapy results in continued intestinal lengthening, with 14 days of therapy producing approximately 80% lengthening—more than doubling the current rates of operative lengthening procedures. Future work must investigate how long enterogenesis can be maintained, and how its efficacy changes with time. In the current study, for example, the lengthening rate decreased slightly from 1.5±0.2 cm/day to 1.2±0.2 cm/day as distraction duration increased from 7 to 14 days. It is possible that more efficient enterogenesis may be maintained during prolonged therapy by increasing distractive force with time, or by the addition of a trophic growth factor during the period of distraction enterogenesis. It is unclear whether ongoing distraction will produce indefinite lengthening, because the maximum duration over which enterogenesis can be achieved has not been evaluated to date. With the current device, however, prolonged distraction beyond 14 days may be limited, because ongoing catheter advancement may be constrained by limited abdominal domain.

The percent length gain of the full distracted segment demonstrated limited variance, with a standard deviation of <10% after 7 and 14 days of distraction. It is notable, however, that the variance in lengthening was considerably greater along the length of the Roux limb, with percent lengthening ranging from 25% (marker 2) to 84% (marker 9) at different points along the bowel. However, after the 10th marker, all Roux limbs had completed their first mesenteric curvature, which may explain why the variance in lengthening outcomes decreased abruptly after this point.

The current method of distraction enterogenesis demonstrated a favorable safety profile with no intestinal ischemia, perforation, or obstruction. Histologic examination of the mucosa at device contact sites did show villus blunting, which may suggest some degree of mild injury; however, this histologic finding may simply reflect the fact that the device was used in unfed intestine. Restoration of feeding after distraction has been shown to restore villus height, 16 and these changes may be prevented if distracting fed bowel.

Defining parameters of safe distraction will be necessary before clinical use. We verified a safe level of initial distraction by using laser Doppler measurement of tissue perfusion along the antimesenteric border of the intestine in the region of device attachment. We found no decrease in perfusion at the time of initial placement of the device or at explant. Although laser Doppler flowmetry has been used to measure acute changes in intestinal tissue perfusion in animal models, it is most sensitive when applied to direct mucosal measurement, which was not possible in this study during device actuation. Direct measurement of tissue perfusion was possible only at the time of implant and explant, when the serosal surface of the intestine could be accessed. Although measurement of perfusion at implant was used to set the initial tension of the device, we could not verify that this tension was maintained after closure of the abdomen. Therefore, we used a distance based distraction regimen of 1 cm advancement of the device per day, which was chosen based on previous success with end-abutment devices. A more robust parameter of distraction would be direct measurement of applied bowel tension, which could be used to guide safe clinical use. For example, development of a pressure sensor to provide continuous measurement of force applied to the bowel wall would allow nasoenteric or trans-stomal placement of a distraction enterogenesis device and nonoperative calibration of distractive force throughout therapy.

The animal model used in this study had the advantage of being similar in size to the human equivalent of a 25- to 50-kg child with SBS; however, the model was limited by requiring a laparotomy for implantation. This model differed from the envisioned clinical use, wherein creation of an enterostomy would be performed as indicated for the clinical scenario, and placement of the device via the stoma would be performed at a later time. In this model, however, the device was placed at the initial laparotomy in order to place bowel markers for measurement of lengthening outcomes. At the time of explant on either postoperative day 7 or 14, generalized formation of intraperitoneal adhesions had occurred. Therefore, lengthening outcomes were measured relative to a marked fed control segment which was exposed to the same postoperative peritoneal environment to control for changes in bowel length due to postoperative inflammation. In future studies and clinical use, markers may be replaced with serial contrast studies to measure the outcomes of enterogenesis.

Another limitation of the operative model used was the placement of the device into an unfed segment of the jejunal Roux limb. Although the target patient population for distraction enterogenesis will be dependent on parenteral nutrition, it will be critical to demonstrate that a clinically applicable device can produce intestinal lengthening in nondiverted bowel without causing obstruction. In prior studies using the current model, a segment of unfed intestine without distraction was used as a secondary control. This approach was not performed in this study, because the device occupied the length of the Roux limb. In this study, distracted bowel was unfed, while the control bowel was fed. Therefore, it is possible that distraction of the fed intestine may result in even greater gains in length in the future.

A potential limitation of the present teachings was the small number of animals that underwent device implantation. The lengthening outcomes of this approach were reproducible, with limited variation in percent length gain between animals. The consistent performance of this device allowed for the demonstration of substantial length gains, despite the limited number of animals.

Although trans-stomal distraction enterogenesis via geometric attachment was shown to be effective, this strategy may be applicable clinically in only select scenarios. First, this device requires direct enteral access to the segment of intestine to be distracted. In contrast to a more flexible device with focal intestinal attachments, the current approach would not be applicable via transgastric or trans-oral placement. Also, this method of intestinal coupling relies on the mesenteric curvature of the small bowel. In patients with severely shortened bowel, the remaining small intestine may not include a mesenteric curve to allow device attachment. In addition, pre-existing adhesions may fix the bowel in a linear orientation, preventing geometric attachment. Focal intestinal attachments, where the specific site of device anchoring can be selected, may be preferable in these scenarios.

In conclusion, the present teachings demonstrated a trans-stomal endoluminal intestinal-lengthening device. Intestinal lengthening was achieved using a novel method of geometric device attachment, with outcomes comparable with operative lengthening. This attachment is an important component in the design of a device for treating patients with SBS.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An indwelling device for insertion in a biological tubular structure, the indwelling device comprising:
   an elongated device having a body and opposing ends, the body having a bending stiffness transverse to a longitudinal axis that is greater than a stiffness of the biological tubular structure; and
   an atraumatic tip member having a proximal end and a distal end, the proximal end extending from at least one of the opposing ends of the elongated device, the proximal end having a first bending stiffness transverse to a longitudinal axis and the distal end having a second bending stiffness transverse to the longitudinal axis, the second bending stiffness being less than the first bending stiffness,
   wherein the elongated device comprises an actuation mechanism to selectively elongate the elongated device from a first length to a second length, the second length being longer than the first length,
   wherein the elongated device comprises a pair of expanding devices disposed on the opposing ends of the elongated device, the pair of expanding devices being actuatable between a retracted position and an extended position to permit application of a tensile load to the biological tubular structure when the elongated device is in the second length.

2. The indwelling device according to claim 1 wherein the first bending stiffness of the proximal end of the atraumatic tip member is generally equal to the bending stiffness of the body of the elongated device.

3. The indwelling device according to claim 1 wherein the second bending stiffness of the distal end of the atraumatic tip member is generally equal to the stiffness of the biological tubular structure.

4. The indwelling device according to claim 1 wherein the second bending stiffness of the distal end of the atraumatic tip member is sufficiently low to prevent damage to tissue of the biological tubular structure.

5. The indwelling device according to claim 1 wherein the second bending stiffness of the distal end of the atraumatic tip member is less than the stiffness of the biological tubular structure.

6. The indwelling device according to claim 1 wherein the atraumatic tip member is deflectable transversely along the longitudinal axis in response to contact with the biological tubular structure.

7. The indwelling device according to claim 1 wherein the proximal end of the atraumatic tip member has a first cross-sectional shape and the distal end of the atraumatic tip member has a second cross-sectional shape, the second cross-sectional shape being less than the first cross-sectional shape.

8. The indwelling device according to claim 1 wherein the atraumatic tip member is uniformly tapered in cross-section from the proximal end to the distal end.

9. The indwelling device according to claim 1 wherein the atraumatic tip member comprises:

a flexure member having a decreasing stiffness along a length thereof; and a cover member surrounding and enclosing the flexure member.

10. The indwelling device according to claim 9 wherein the flexure member has a varying cross-sectional shape along the length thereof.

11. The indwelling device according to claim 1 wherein the elongated device comprises a friction enhancement engageable with an interior surface of the biological tubular structure.

12. The indwelling device according to claim 11, wherein the friction enhancement comprises a plurality of ridges fixed to the expanding devices which engage with the interior surface of the biological tubular structure.

13. The indwelling device according to claim 11 wherein the friction enhancement comprises a fenestrated decoupling system generally preventing contact of the friction enhancement with the interior surface of the biological tubular structure when the elongated device is in the first length, the fenestrated decoupling system generally permitting contact of the friction enhancement with the interior surface of the biological tubular structure when the elongated device is in the second length.

14. The indwelling device according to claim 13, wherein the fenestrated decoupling system comprises a plurality of fenestrated elastic bands having a spaced-apart configuration extending generally along a longitudinal length of the elongated device.

* * * * *

UNITED STATES PATENT AND TRADEMARK OFFICE
CERTIFICATE OF CORRECTION

PATENT NO. : 10,117,738 B2
APPLICATION NO. : 15/005218
DATED : November 6, 2018
INVENTOR(S) : Farokh R. Demehri et al.

Page 1 of 1

It is certified that error appears in the above-identified patent and that said Letters Patent is hereby corrected as shown below:

In the Specification

Column 1, Line 17, under "Government Interest," delete "This invention was made with government support under FD003787 awarded by the Food and Drug Administration. The government has certain rights in the invention." and insert --This invention was made with government support under FD003787 awarded by the National Institutes of Health. The government has certain rights in the invention.-- therefor.

Signed and Sealed this
Nineteenth Day of February, 2019

Andrei Iancu
*Director of the United States Patent and Trademark Office*